United States Patent
Huang et al.

(10) Patent No.: US 11,642,333 B2
(45) Date of Patent: May 9, 2023

(54) INHALABLE FORMULATION OF A SOLUTION CONTAINING VILANTEROL TRIFENATATE AND UMECLIDINIUM BROMIDE

(71) Applicant: ANOVENT PHARMACEUTICAL (U.S.), LLC, Newark, NJ (US)

(72) Inventors: Cai Gu Huang, Shrewsbury, MA (US); Ying Ai Xu, Shanghai (CN); Yue Zhao, Shanghai (CN); Hui Yuan, Shanghai (CN)

(73) Assignee: ANOVENT PHARMACEUTICAL (U.S.), LLC, Newark, NJ (US)

(*) Notice: Subject to any disclaimer, the term of this patent is extended or adjusted under 35 U.S.C. 154(b) by 337 days.

(21) Appl. No.: 16/881,354

(22) Filed: May 22, 2020

(65) Prior Publication Data

US 2020/0368214 A1    Nov. 26, 2020

Related U.S. Application Data

(60) Provisional application No. 62/851,672, filed on May 23, 2019.

(51) Int. Cl.
  *A61K 31/439* (2006.01)
  *A61K 9/00* (2006.01)
  *A61K 31/137* (2006.01)

(52) U.S. Cl.
  CPC .......... *A61K 31/439* (2013.01); *A61K 9/0078* (2013.01); *A61K 31/137* (2013.01)

(58) Field of Classification Search
  CPC .... A61K 31/138; A61K 47/12; A61K 47/186; A61K 47/26; A61K 47/40; A61K 31/439; A61K 9/0078; A61K 31/137; A61P 11/06
  See application file for complete search history.

(56) References Cited

U.S. PATENT DOCUMENTS

| | | | |
|---|---|---|---|
| 6,890,517 | B2 | 5/2005 | Drechsel et al. |
| 9,474,747 | B2 | 10/2016 | Albrecht et al. |
| 9,750,726 | B2 | 9/2017 | Baker et al. |
| 2014/0308214 | A1 | 10/2014 | Malhotra et al. |
| 2019/0030268 | A1 | 1/2019 | Huang |

FOREIGN PATENT DOCUMENTS

WO    03024439 A1    3/2003

OTHER PUBLICATIONS

Alangari AA. Corticosteroids in the treatment of acute asthma. Ann Thorac Med.; 9(4):187-192. (Year: 2014).*
Mehri, et al., "Aerosol Deposition Measurements with ODAPT Mask Adapter", Respiratory Theory, 2018, vol. 13, No. 2,p. 10-14, Table 2 under 'MMAD'.
Ziegler, et al., "Comparison of Cascade Impaction and Laser Diffraction for Particle Size Distribution Measurements", Journal of Aerosol Medicine, 2005, vol. 18, No. 3, p. 311-324, p. 314 first paragraph.
Search Report for related application PCT/US20/34216, dated Aug. 28, 2020.
Written Opinion of the International Searching Authority for related application PCT/US20/34216, dated Aug. 28, 2020.

* cited by examiner

*Primary Examiner* — Sahar Javanmard
(74) *Attorney, Agent, or Firm* — Parker Poe Adams & Bernstein (57) ABSTRACT

The present invention relates to a liquid, propellant-free pharmaceutical preparation and a method for administering a pharmaceutical preparation by nebulizing the pharmaceutical preparation in an inhaler. The propellant-free pharmaceutical preparation comprises: (a) an active substance selected from umeclidinium bromide and vilanterol trifenatate and combinations thereof; (b) a solvent; (c) a pharmacologically acceptable solubilizing agent; and (d) a pharmacologically acceptable preservative, and optionally includes a pharmacologically acceptable stabilizer, a pharmacologically acceptable co-solvent, or other pharmacologically acceptable additives.

24 Claims, 8 Drawing Sheets

INHALABLE FORMULATION OF A SOLUTION CONTAINING VILANTEROL TRIFENATATE AND UMECLIDINIUM BROMIDE

PRIORITY STATEMENT

This application claims the benefit of U.S. Provisional Patent Application No. 62/851,672, filed on May 23, 2019, which is incorporated herein by reference in its entirety.

BACKGROUND OF THE INVENTION

Vilanterol trifenatate, chemically 4-{(1R)-2-[(6-(2-((2,6-dichlorobenzyl) oxy) ethoxy) hexyl) amino]-1-hydroxy-ethyl}-2-(hydroxymethyl) phenol mono (2,2,2-triphenylacetate) disclosed in WO03024439, has the following chemical structure:

Umeclidinium bromide, chemically 1-[2-(Benzyloxy) ethyl]-4-(hydroxydiphenylmethyl)-1-azoniabicyclo [2.2.2] octane bromide disclosed in WO2014027045, has the following chemical structure:

Umeclidinium bromide is a long-acting muscarinic antagonist (LAMA) approved for the maintenance treatment of chronic obstructive pulmonary disease (COPD). In chronic obstructive pulmonary disease, acetylcholine is released to airway smooth muscle and acts reversibly through postsynaptic muscarinic receptors to mediate airway smooth muscle contraction and mucus secretion. Inhaled anticholinergic agents can block muscarinic receptors on airway smooth muscle to inhibit bronchoconstriction.

Vilanterol trifenatate is another long-acting muscarinic antagonist that activates beta-2 adrenoreceptors on airway smooth muscle, causing bronchodilation. Beta-2 receptors are the adrenergic receptors in bronchial smooth muscle.

These two compounds have valuable pharmacological properties. Vilanterol trifenatate and umeclidinium bromide can provide therapeutic benefit in the treatment of asthma or chronic obstructive pulmonary disease, including chronic bronchitis and emphysema.

Umeclidinium bromide has a poor oral bioavailability. The combination of umeclidinium bromide and vilanterol trifenatate is currently administered as an inhalable dry powder formulation, which is disclosed in U.S. Pat. No. 9,750,726. The dry powder inhalation formulation typically has about 20-30% lung deposition due to inherent variations and characteristics of the dry powder and administration devices.

The present invention relates to a propellant-free inhalable formulation of a pharmaceutically acceptable salt of vilanterol, such as vilanterol trifenatate, and a pharmaceutically acceptable salt of umeclidinium, such as umeclidinium bromide, dissolved in water or a mixture of water and ethanol, in conjunction with active substances preferably administered by soft mist or nebulization inhalation devices, and propellant-free inhalable aerosols resulting therefrom. The pharmaceutical formulations disclosed in the current invention are especially suitable for soft mist inhalation or nebulization inhalation, which have much better lung depositions (typically up to 55-60%), compared to the dry powder inhalation method.

The pharmaceutical formulation of the present invention is particularly suitable for administering active substances by soft mist or nebulization inhalation, especially for treating asthma and chronic obstructive pulmonary disease.

SUMMARY OF THE INVENTION

Aspects and advantages of the invention will be set forth in part in the following description, or may be obvious from the description, or may be learned through practice of the invention.

The present invention relates to pharmaceutical formulations of umeclidinium and vilanterol, and their pharmaceutically acceptable salts or solvates, such as umeclidinium bromide and vilanterol trifenatate, which can be administered by soft mist or nebulization inhalation. The pharmaceutical formulations according to the invention meet high quality standards.

One aspect of the present invention is to provide an aqueous pharmaceutical formulation containing vilanterol trifenatate and umeclidinium bromide, which meets the high standards needed in order to be able to achieve optimum nebulization of a solution using the inhalers mentioned hereinbefore. A pharmaceutically stable pharmaceutical formulation may be stable for a storage time of some years, for example one year, or for example three years.

Another aspect of the invention is to provide propellant-free formulations of solutions containing vilanterol trifenatate and umeclidinium bromide which are nebulized under pressure using an inhaler which may be a soft mist or nebulization inhaler device. Compositions of the invention may be delivered by aerosol having reproducible characteristics within a specified range.

More specifically, another aspect of the invention is to provide stable pharmaceutical formulations of aqueous solutions containing vilanterol trifenatate, umeclidinium bromide, and pharmaceutically acceptable excipients which can be administered by soft mist or nebulization inhalation.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

The use of identical or similar reference numerals in different figures denotes identical or similar features.

DETAILED DESCRIPTION OF THE INVENTION

For purposes of describing the invention, reference now will be made in detail to embodiments and/or methods of the invention, one or more examples of which are illustrated in or with the drawings. Each example is provided by way of explanation of the invention, not limitation of the invention. In fact, it will be apparent to those skilled in the art that various modifications and variations can be made in the present invention without departing from the scope or spirit of the invention. For instance, features or steps illustrated or described as part of one embodiment, can be used with another embodiment or steps to yield a still further embodiments or methods. Thus, it is intended that the present invention covers such modifications and variations as come within the scope of the appended claims and their equivalents.

It is desirable to use a liquid formulation without propellant gases administered using suitable inhalers, in order to achieve a better distribution of active substances in the lung. Furthermore, it is desirable to increase the lung deposition of the drug delivered by inhalation.

Currently, the traditional pMDI or DPI (dry powder inhalation) device can only deliver about 20-30% of drug from a formulation into the lung, resulting in a significant amount of drug deposited in the month and throat, which ends up in the stomach and may cause unwanted side effects and/or secondary absorption through the digestive system.

Therefore, there is a need to improve inhalation drug delivery by increasing lung deposition. The soft mist or nebulization inhalation device disclosed in US20190030268 can significantly increase the lung deposition of inhalable drugs.

Such inhalers can nebulize a small amount of a liquid formulation within a few seconds into an aerosol suitable for therapeutic inhalation. Such inhalers are particularly suitable to administer the liquid formulation of the present invention.

The soft mist or nebulization devices suitable for administering the aqueous pharmaceutical formulation of the present invention are those in which an amount of less than about 70 microliters of pharmaceutical solution can be nebulized in one puff, such as less than about 30 microliters, more particularly less than about 15 microliters, so that the inhalable part of the aerosol corresponds to a therapeutically effective quantity. The average particle size of the aerosol formed from one puff is less than about 15 microns, or less than about 10 microns.

A device of this kind for the propellant-free administration of a metered amount of a liquid pharmaceutical composition for inhalation is described in detail, for example, in US20190030268.

The pharmaceutical formulation solution in the nebulizer is converted into aerosol destined for the lungs. The pharmaceutical solution is sprayed by the nebulizer using high pressure.

In certain inhalers that can be used with the invention, the pharmaceutical solution is stored in a reservoir. In an embodiment, the pharmaceutical solution formulations of the invention do not contain any ingredients which might interact with the inhaler to affect the pharmaceutical quality of the formulation or of the aerosol produced. In an embodiment, the pharmaceutical formulations of the invention are very stable when stored and can be administered directly.

In an embodiment, the pharmaceutical solution formulations of the current invention contain additives, such as the disodium salt of edetic acid (sodium edetate), to reduce the incidence of spray anomalies and to stabilize the formulation solutions. In an embodiment, the aqueous pharmaceutical solution formulations of the invention have a low concentration of sodium edetate.

Therefore, one aspect of the present invention is to provide an aqueous pharmaceutical formulation containing vilanterol trifenatate and umeclidinium bromide, which meets the high standards needed in order to be able to achieve optimum nebulization of a solution using the inhalers mentioned hereinbefore. In an embodiment, the active substances in the pharmaceutical formulation are stable for a storage time of some years, for example one year, or for example three years.

Another aspect of the current invention is to provide propellant-free formulations of solutions containing vilanterol trifenatate and umeclidinium bromide, which are nebulized under pressure using an inhaler, such as soft mist inhalers or other nebulization inhalers. Compositions of the invention may be delivered by aerosol having reproducible characteristics within a specified range.

Another aspect is to provide an aqueous pharmaceutical solution formulation containing vilanterol trifenatate and umeclidinium bromide and inactive excipients which can be administered by inhalation. According to the invention, any pharmaceutically acceptable salts or solvates of vilanterol and umeclidinium may be used for the formulation. In an embodiment, the salts of vilanterol and umeclidinium are vilanterol trifenatate and umeclidinium bromide. In an embodiment, the active substances are selected from combinations of vilanterol trifenatate and umeclidinium bromide.

In an embodiment, the vilanterol trifenatate and umeclidinium bromide are dissolved in a solvent. The solvent may preferably be a mixture of water and ethanol. Ethanol may be added to the formulation in order to increase the solubility of additives or other active substances. In an embodiment, the relative proportion of ethanol to water is about 5:95 (v/v) to about 30:70 (v/v).

In an embodiment, ethanol is present in the solvent at about 5% to about 30% by volume, more specifically about 10% to about 25% by volume. In one embodiment, ethanol is present in the solvent at about 20% to about 30% by volume. In another embodiment, the pharmaceutical preparation contains a single solvent.

The concentration of the vilanterol trifenatate and umeclidinium bromide in the finished pharmaceutical preparation depends on the desired therapeutic effects, and can be determined by a person of ordinary skill in the art. In an embodiment, the concentration of vilanterol trifenatate in the formulation is between about 5 mg/100 ml and about 40 mg/100 ml, more specifically between about 8 mg/100 ml and about 30 mg/100 ml. In an embodiment, the concentration of umeclidinium bromide is between about 10 mg/100 ml and about 80 mg/100 ml, more specifically between about 15 mg/100 ml and about 50 mg/100 ml.

In formulations according to the invention, if desired, edetic acid (EDTA) or one of the known salts thereof, disodium edetate or edetate disodium dihydrate, may be added as a stabilizer or complexing agent. In an embodiment, the formulation of the invention contains edetic acid and/or a salt or salts thereof. Other comparable stabilizers or complexing agents can be used in the present invention. Such other stabilizers or complexing agents include, for example, citric acid, edetate disodium, and edetate disodium dihydrate. In the present invention, complexing agents are molecules which are capable of entering into complex bonds. In an embodiment, complexing agents have the effect of complexing cations.

The concentration of the stabilizer or complexing agents is about 5 mg/100 ml to about 30 mg/100 ml. In an embodiment, the concentration of the stabilizer or complexing agents is about 10 mg/100 ml to about 25 mg/100 ml. In one embodiment, the concentration of edetate disodium dihydrate is about 11 mg/100 ml to about 22 mg/100 ml. More specifically, in an embodiment, the concentration range is from about 11 mg/100 ml to less than about 20 mg/100 ml. In another embodiment, the concentration of edetate disodium dihydrate is about 11 mg/100 ml.

In an embodiment of the invention, vilanterol trifenatate and umeclidinium bromide are present in solution in the pharmaceutical formulation. In another embodiment, all the ingredients of the formulation are present in solution.

In addition to ethanol, other co-solvents may be added to the formulation according to the invention. In an embodiment, other co-solvents are those which contain hydroxyl groups or other polar groups, such as alcohols, isopropyl alcohol, propylene glycol, polyethylene glycol, polypropylene glycol, glycerol, and polyoxyethylene alcohols. In an embodiment, the pharmaceutical formulation contains only water and ethanol as solvents, with no additional co-solvents.

In the present invention, additives include any pharmacologically acceptable and/or therapeutically useful substance that is not an active substance but that can be formulated together with the active substances in a pharmacologically suitable solvent, in order to improve the qualities of the pharmaceutical formulation. In an embodiment, the additives have no pharmacological effects or no appreciable or at least no undesirable pharmacological effects in the context of the desired therapy. The additives include, for example, other stabilizers, complexing agents, antioxidants, surfactants, and/or preservatives which prolong the shelf life of the finished pharmaceutical formulation, vitamins and/or other additives known in the art. In an embodiment, the pharmaceutical formulation contains a preservative and no other additives.

In an embodiment, the formulations according to the invention include suitable surfactants, which may function as solubilizing agents. The solubilizing agents include pharmacologically acceptable substances, In an embodiment, the solubilizing agents are selected from surfactants such as, for example, tween-80, poloxamer, polyoxyethylated castor oil, polyethylene glycol, solutol HS 15, and polyvinylpyrrolidone.

In one embodiment, the surfactant concentration is less than about 180 mg/100 ml, more particularly from about 20 mg/100 ml to less than about 180 mg/100 ml. In another embodiment, the content of surfactant tween-80 is about 40 to about 180 mg/100 ml. In other embodiments, the content of surfactant tween-80 is about 20 to about 40 mg/100 ml. In another embodiment, the quantity of surfactant is about 20 mg to about 180 mg/100 ml, such as between about 20 mg/100 ml and about 100 mg/100 ml, more particularly between about 20 mg/100 ml and about 80 mg/100 ml.

Suitable preservatives can be added to protect the formulation from contamination with pathogenic bacteria. Preservatives comprise, for example, benzalkonium chloride or benzoic acid or sodium benzoate. In an embodiment, the pharmaceutical formulation contains only benzalkonium chloride as a preservative. In an embodiment, the preservative is present in an amount of about 10 mg/100 ml to about 50 mg/100 ml. In another embodiment, benzalkonium chloride is present in an amount of about 20 mg/100 ml to about 30 mg/100 ml.

To produce the propellant-free aerosols according to the invention, the pharmaceutical formulations containing vilanterol trifenatate and umeclidinium bromide according to the invention may be used in an inhaler of the kind described hereinbefore.

A further developed embodiment of the preferred inhaler or atomizer is disclosed in US20190030268, which is incorporated by reference. This soft mist nebulizer can be used to produce the inhalable aerosols according to the invention.

The inhalation device can be carried anywhere by a patient, having a cylindrical shape and convenient size of less than about 8 cm to about 18 cm long, and about 2.5 cm to about 5 cm wide. The nebulizer sprays a defined volume of the pharmaceutical formulation out through small nozzles at high pressures, so as to produce inhalable aerosols.

Figure 1:
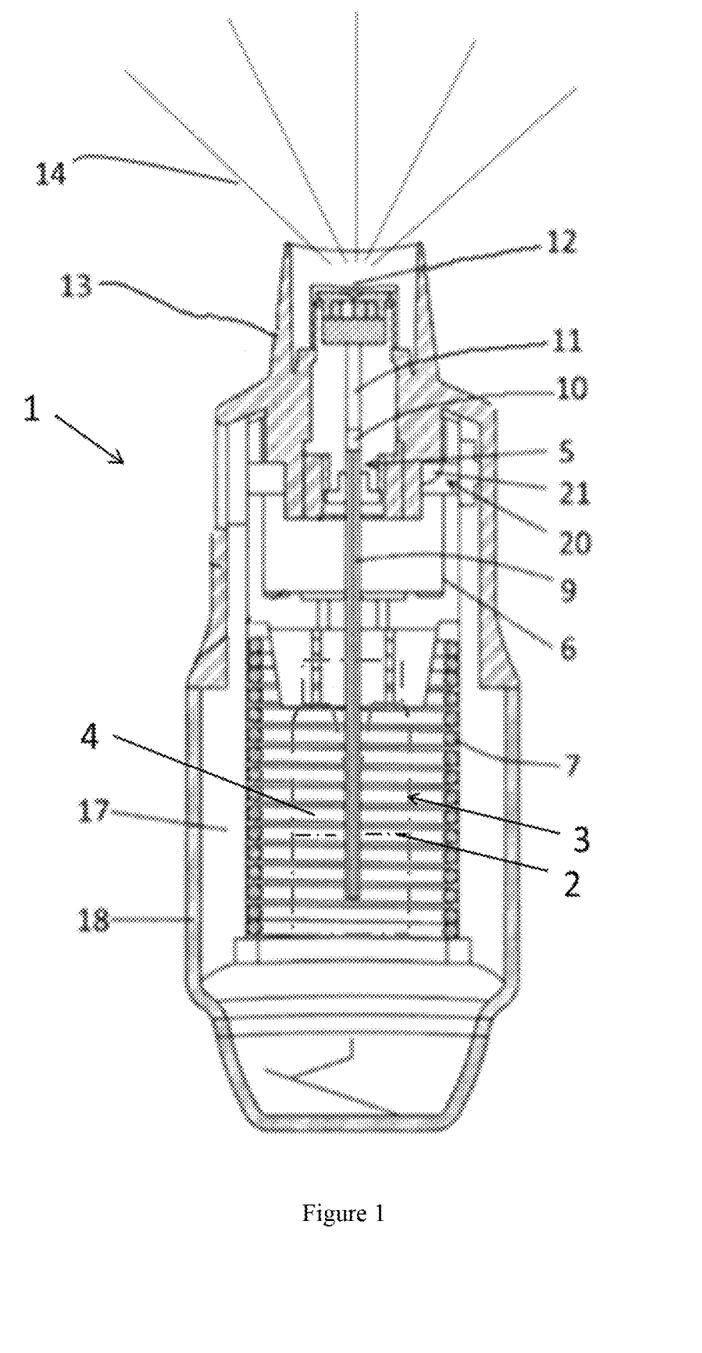
FIG. 1 shows a longitudinal section through an atomizer in the stressed state.

FIG. 1 shows a longitudinal section through the atomizer comprising a block function and a counter in the stressed state. In an embodiment, the inhalation device comprises an atomizer 1, a fluid 2, a vessel 3, a fluid compartment 4, a pressure generator 5, a holder 6, a drive spring 7, a delivering tube 9, a non-return valve 10, pressure room 11, a nozzle 12, a mouthpiece 13, an aerosol 14, an air inlet 15, an upper shell 16, and an inside part 17.

The inhalation atomizer 1 comprising a block function and a counter described above for spraying a medicament fluid 2, such as a pharmaceutical formulation of the invention, is demonstrated in FIG. 1 in the stressed state. The atomizer 1 described above is a propellant-free portable inhaler.

For the typical atomizer 1 described above, an aerosol 14 that can be inhaled by a patient is generated through the atomization of the fluid 2, which in an embodiment, is a pharmaceutical formulation of the invention. The pharmaceutical formulation is typically administered at least once a day, more specifically multiple times a day, preferred at predestined time gaps, according to how serious the illness affects the patient.

In an embodiment, the atomizer 1 described above has a substitutable and insertable vessel 3, which contains a medicament fluid 2. Therefore, a reservoir for holding the fluid 2 is formed in the vessel 3. Specifically, the medicament fluid 2 is located in the fluid compartment 4 formed by a collapsible bag in the vessel 3.

In an embodiment, the amount of fluid 2 for the inhalation atomizer 1 described above can provide an adequate amount for a patient, such as up to about 200 doses. In an embodiment, vessel 3 has a volume of about 2 ml to about 10 ml. A pressure generator 5 in the atomizer 1 is used to deliver and atomize the fluid 2, specifically in a predestined dosage amount. The fluid 2 is released and sprayed in individual doses, such as from about 5 to about 30 microliters.

In an embodiment, the atomizer 1 described above may have a pressure generator 5 and a holder 6, a drive spring 7, a delivering tube 9, a non-return valve 10, a pressure room 11, and a nozzle 12 in the area of a mouthpiece 13. The vessel 3 is latched by the holder 6 in the atomizer 1 so that the delivering tube 9 is plunged into the vessel 3. The vessel 3 may be separated from the atomizer 1 for substitution.

In an embodiment, when drive spring 7 is stressed in axial direction, the delivering tube 9 and the vessel 3 along with the holder 6 will be shifted downwards. Then the fluid 2 will be sucked into the pressure room 11 through delivering tube 9 and the non-return valve 10.

In an embodiment, after releasing the holder 6, the stress is eased. During this process, the delivering tube 9 and closed non-return valve 10 are shifted back upward by releasing the drive spring 7. Consequently, the fluid 2 is under the pressure in the pressure room 11. Then the fluid 2 is pushed through the nozzle 12 and atomized into an aerosol 14 by the pressure. A patient may inhale the aerosol 14 through the mouthpiece 13, while the air is sucked into the mouthpiece 13 through air inlets 15.

In an embodiment, the inhalation atomizer 1 described above has an upper shell 16 and an inside part 17, which may be rotated relative to the upper shell 16. A lower shell 18 is manually operable to attach onto the inside part 17. The lower shell 18 may be separated from the atomizer 1 so that the vessel 3 may be substituted and inserted.

In an embodiment, the inhalation atomizer 1 described above may have a lower shell 18, which carries the inside part 17, and which is rotatable relative to the upper shell 16. As a result of rotation and engagement between the upper unit 17 and the holder 6, through a gear 20, the holder 6 is axially moved the counter to the force of the drive spring 7 and the drive spring 7 is stressed.

In an embodiment in the stressed state, the vessel 3 is shifted downwards and reaches a final position, which is demonstrated in FIG. 1. The drive spring 7 is stressed under this final position. Then the holder 6 is clasped. The vessel 3 and the delivering tube 9 are prevented from moving upwards so that the drive spring 7 is stopped from easing.

In an embodiment, the atomizing process occurs after releasing the holder 6. The vessel 3, the delivering tube 9, and the holder 6 are shifted back by the drive spring 7 to the beginning position. This shifting is referred to as major shifting. While the major shifting occurs, the non-return valve 10 is closed and the fluid 2 is under the pressure in the pressure room 11 by the delivering tube 9, and then the fluid 2 is pushed out and atomized by the pressure.

In an embodiment, the inhalation atomizer 1 described above may have a clamping function. During the clamping, the vessel 3 performs a lifting shift or for the withdrawal of the fluid 2 during the atomizing process. The gear 20 has sliding surfaces 21 on the upper shell 16 and/or on the holder 6, which may make holder 6 move axially when the holder 6 is rotated relative to the upper shell 16.

In an embodiment, the holder 6 is not blocked for too long and can carry on the major shifting. The fluid 2 is pushed out and atomized.

In an embodiment, when the holder 6 is in the clamping position, the sliding surfaces 21 move out of engagement. Then the gear 20 releases the holder 6 for the opposite axial shift.

Figure 2:
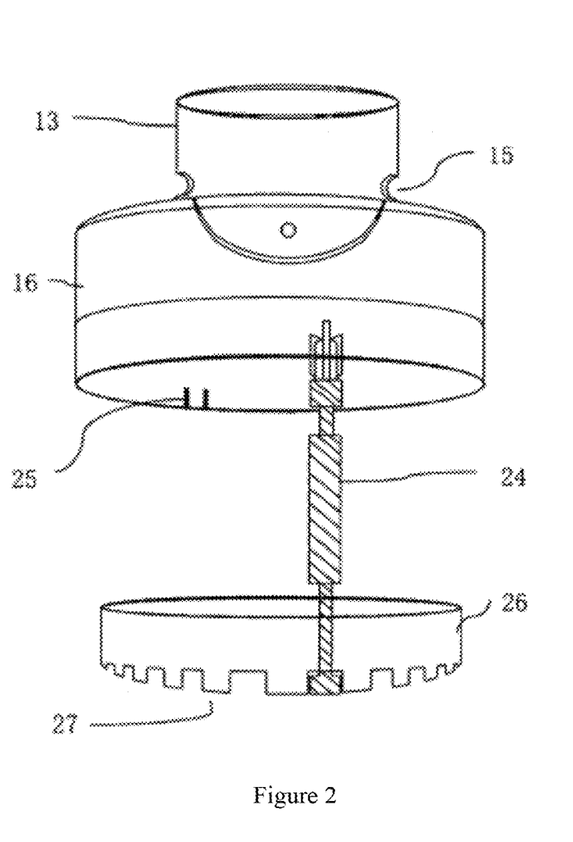
FIG. 2 shows a counter element of the atomizer.
Figure 3:
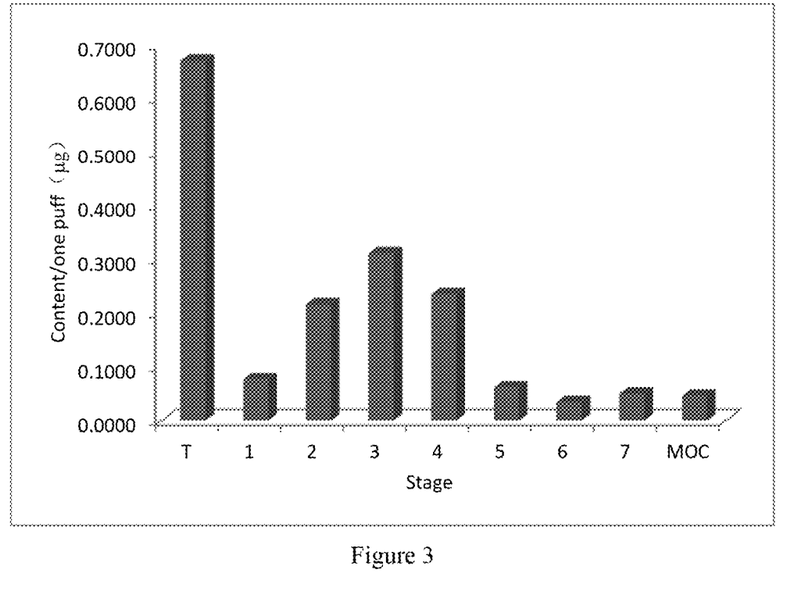
FIG. 3 shows aerodynamic particle size distribution of vilanterol trifenatate in example 5.
Figure 4:
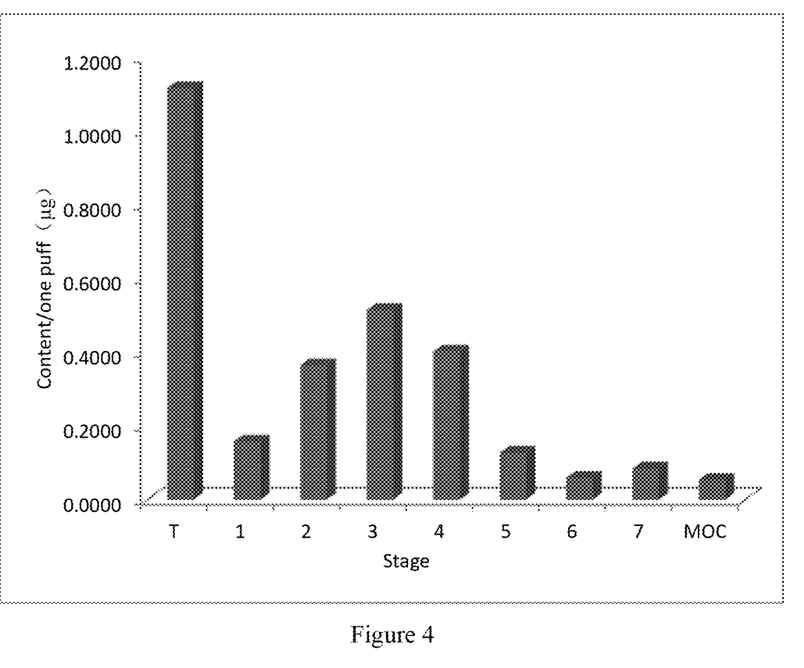
FIG. 4 shows aerodynamic particle size distribution of umeclidinium bromide in example 5.
Figure 5:
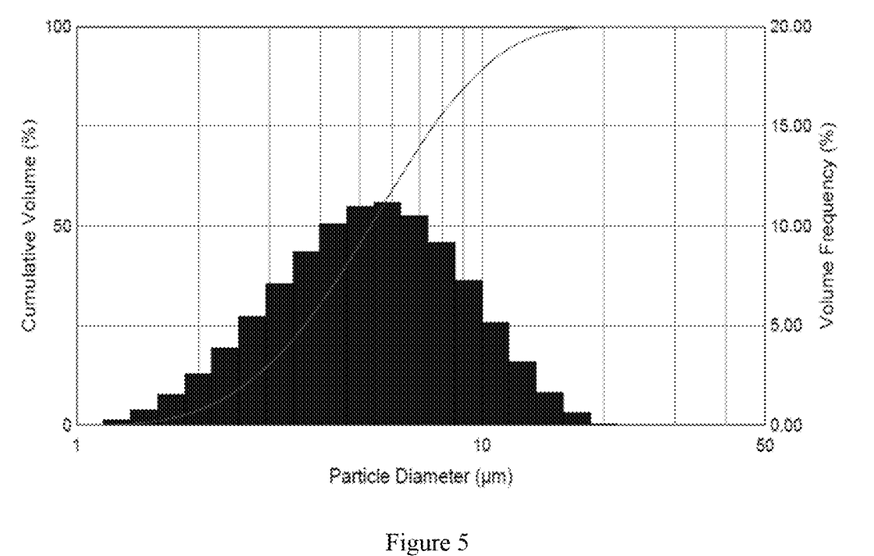
FIG. 5 shows sample III particle size distribution of droplets sprayed by soft mist inhaler in example 6.
Figure 6:
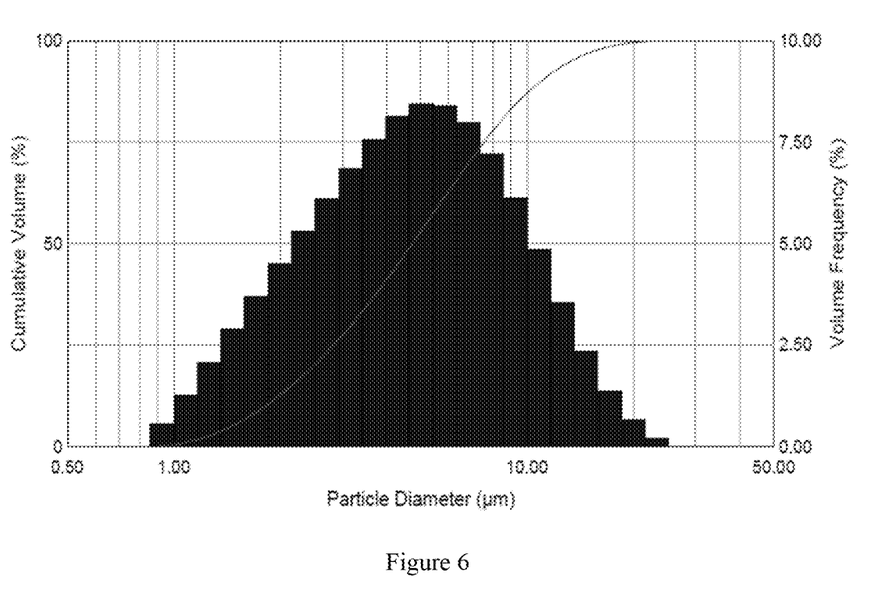
FIG. 6 shows sample III particle size distribution of droplets sprayed by compressed air nebulizer in example 6.
Figure 7:
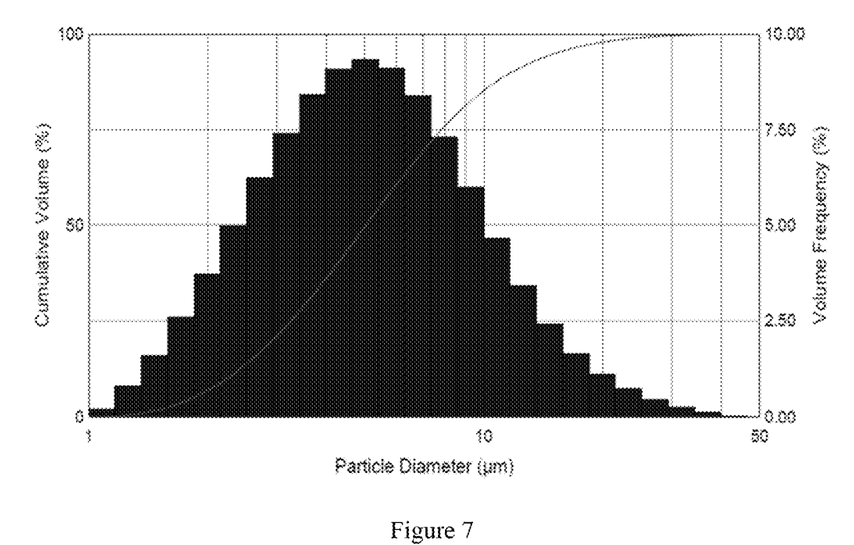
FIG. 7 shows sample III particle size distribution of droplets sprayed by ultrasonic vibrating mesh nebulizer in example 6.
Figure 8:
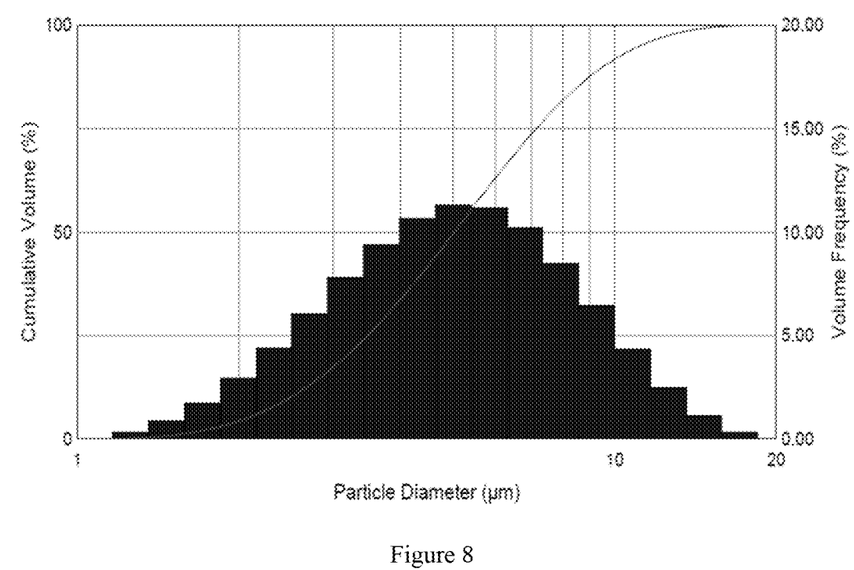
FIG. 8 shows sample IV particle size distribution of droplets sprayed by soft mist inhaler in example 6.
Figure 9:
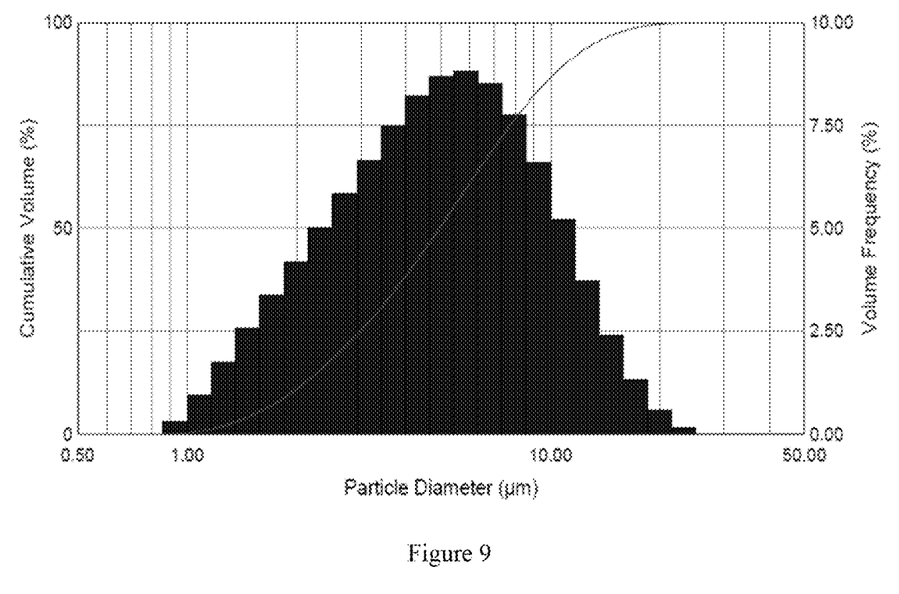
FIG. 9 shows sample IV particle size distribution of droplets sprayed by compressed air nebulizer in example 6.
Figure 10:
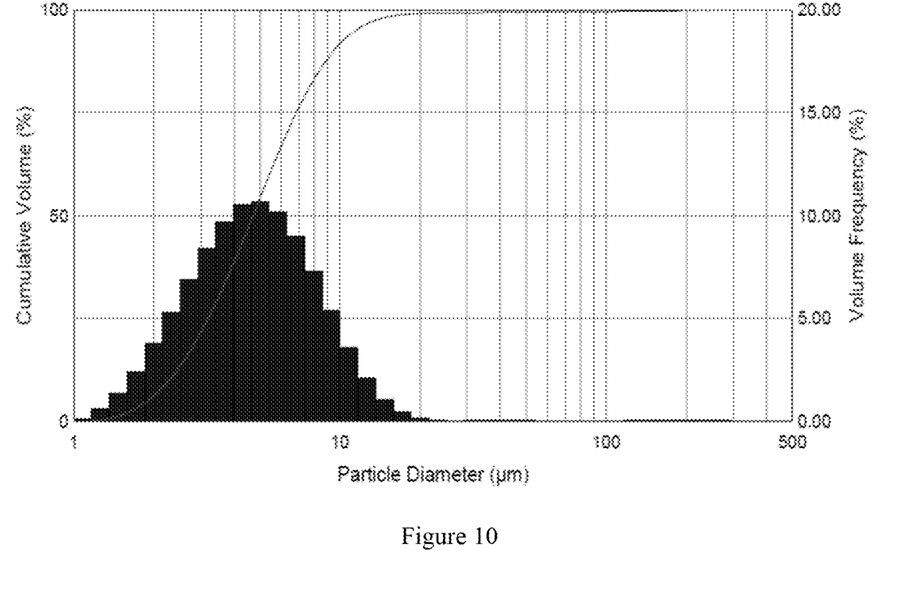
FIG. 10 shows sample IV particle size distribution of droplets sprayed by ultrasonic vibrating mesh nebulizer in example 6.
Figure 11:
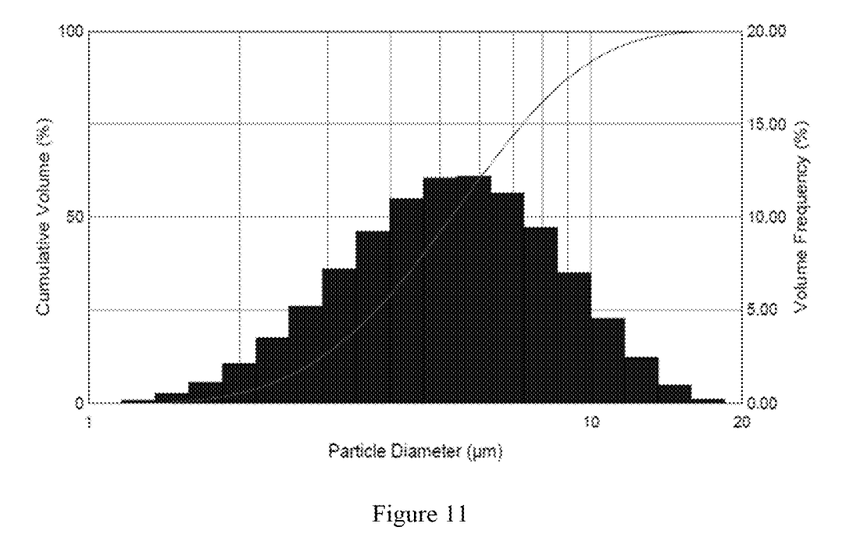
FIG. 11 shows sample V particle size distribution of droplets sprayed by soft mist inhaler in example 6.
Figure 12:
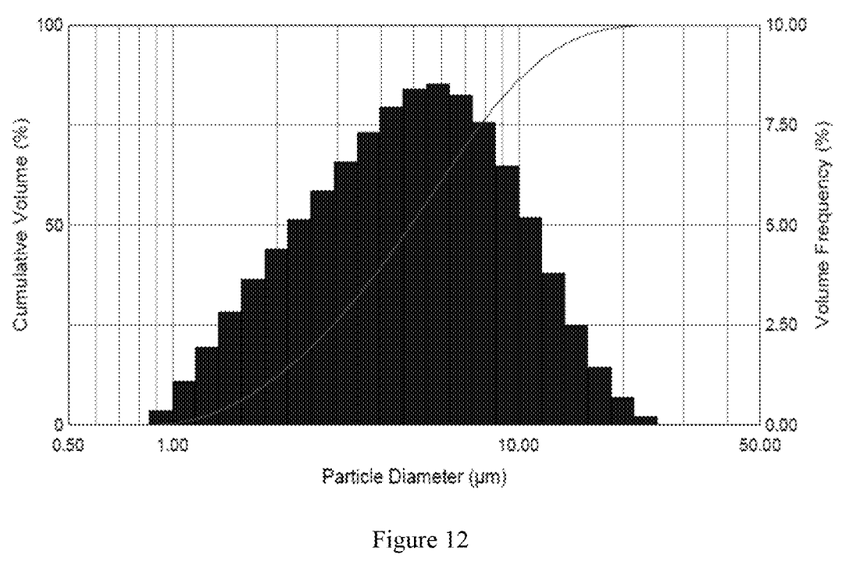
FIG. 12 shows sample V particle size distribution of droplets sprayed by compressed air nebulizer in example 6.
Figure 13:
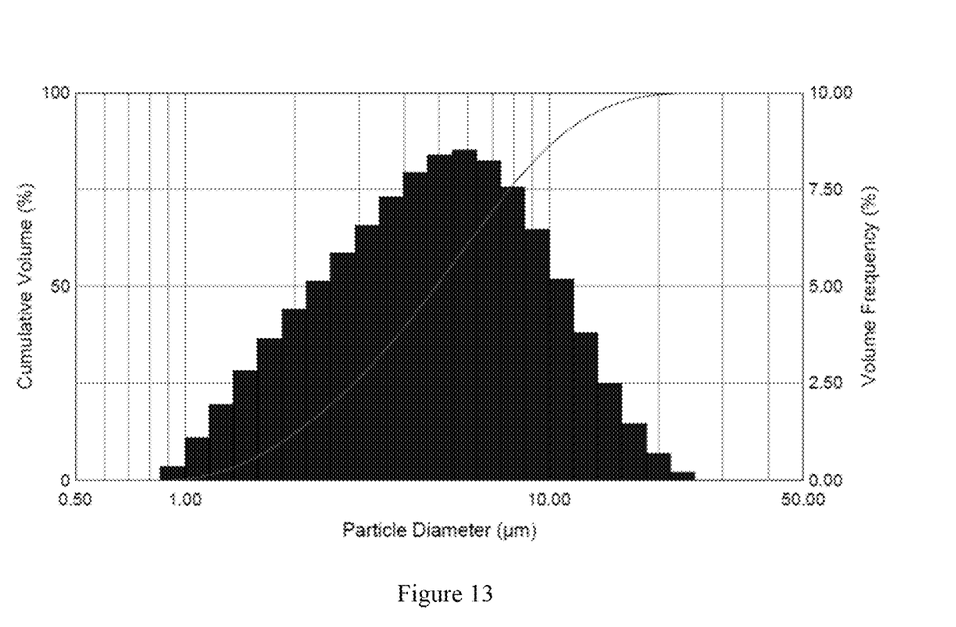
FIG. 13 shows sample V particle size distribution of droplets sprayed by ultrasonic vibrating mesh nebulizer in example 6.

In an embodiment, the atomizer 1 includes a counter element shown in FIG. 2. The counter element has a worm 24 and a counter ring 26. In an embodiment, the counter ring 26 is circular and has a dentate part at the bottom. The worm 24 has upper and lower end gears. The upper end gear contacts with the upper shell 16. The upper shell 16 has inside bulge 25. When the atomizer 1 is employed, the upper shell 16 rotates; and when the bulge 25 passes through the upper end gear of the worm 24, the worm 24 is driven to rotate. The rotation of the worm 24 drives the rotation of the counter ring 26 through the lower end gear. This results in the counting effect.

In an embodiment, the locking mechanism is realized mainly by two protrusions. Protrusion A is located on the outer wall of the lower unit of the inside part. Protrusion B is located on the inner wall of counter. The lower unit of the inside part is nested in the counter. The counter can rotate relative to the lower unit of the inside part. Because of the rotation of the counter, the number displayed on the counter can change as the actuation number increases, and can be observed by the patient. After each actuation, the number displayed on the counter changes. Once the predetermined number of actuations is achieved, Protrusion A and Protrusion B will encounter each other and the counter will be prevented from further rotation. This blocks the atomizer, stopping it from further use. The number of actuations of the device can be counted by the counter.

The nebulizer described above is suitable for nebulizing the pharmaceutical preparations according to the invention to form an aerosol suitable for inhalation. Nevertheless, the formulation according to the invention can also be nebulized using other inhalers apart from those described above, such as ultrasonic vibrating mesh nebulizers and compressed air nebulizers.

EXAMPLES

Materials and reagents:
Tween—80 purchased from Nanjing Wei Er Chemical Co., Ltd,
Ethanol purchased from Nanjing reagent Co., Ltd,
50% benzalkonium chloride purchased from Spectrum Pharmaceuticals Inc,
Edetate disodium dihydrate purchased from Nanjing reagent Co., Ltd;

Example 1

The synthesis of umeclidinium bromide:
1-azabicyclo [2.2.2] oct-4-yl(diphenyl)methanol (50.0 g, 0.170 mol) was obtained by the method disclosed in WO2014027045. 1-azabicyclo [2.2.2] oct-4-yl(diphenyl)methanol and benzyl 2-bromoethyl ether (40.2 g, 0.187 mol) were dissolved with n-propanol (500 ml), and refluxed for 13 hours. Then cooled to room temperature and stirred for 6 hours. The product was filtered and washed with n-propanol, and then vacuum dried at 50° C. to give a white solid (73.7 g, 0.145 mol). The yield of umeclidinium bromide was 85.0%, and HPLC purity was 99.0%.

The synthesis of vilanterol trifenatate:
4-((R)-2-{6-[2-(2,6-dichlorobenzyloxy)-ethoxy]-hexylamino}-1-hydroxyethyl-)-2-hydroxymethyl-phenol (10.0 g, 20.5 mmol) was obtained by the method disclosed in USRE44874. Triphenylacetic acid (5.9 g, 20.5 mmol) was added to an ethanol (70 ml) solution containing 4-((R)-2-{6-[2-(2,6-dichlorobenzyloxy)-ethoxy]-hexylamino}-1-hydroxyethyl-)-2-hydroxymethyl-phenol. The mixture was refluxed and stirred for 0.5 hour until dissolved. Then cooled to room temperature and stirred for 6 hours. The product was filtered and washed with ethanol, and then vacuum dried at 50° C. to give a white solid (12.8 g, 16.5 mmol). The yield of vilanterol trifenatate was 80.5%, and HPLC purity was 99.0%.

Example 2

The preparation of sample I and sample II inhalation solution:
The ingredients are listed in table 1. 50% benzalkonium chloride and tween-80 according to table 1, were dissolved in 16 g of 95% ethanol for three times, and then transferred into 100 ml volumetric flask. Vilanterol trifenatate and umeclidinium bromide according to table 1 were added to the solution, and then sonicated until completely dissolved. Edetate disodium dihydrate according to table 1 was added into the solution, and then sonicated until completely dissolved. Finally, the flask was made to volume with purified water. Sample I and sample II solutions remained essentially clear.

The tested results were shown in table 2, which indicated that both vilanterol trifenatate and umeclidinium bromide had been completely dissolved in the solution containing ethanol and tween-80.

TABLE 1

| Ingredient contents of sample I and sample II of 100 ml inhalable formulation | | |
|---|---|---|
| Ingredients | Sample I | Sample II |
| Umeclidinium bromide | 10.5 mg | 73.5 mg |
| Vilanterol trifenatate | 5.5 mg | 38.5 mg |
| Edetate Disodium Dihydrate | 5 mg | 30 mg |
| Tween-80 | 20 mg | 180 mg |
| 50% benzalkonium chloride | 10 mg | 50 mg |
| 95% Ethanol | 20 g | 20 g |
| Purified water | added to 100 ml | added to 100 ml |

TABLE 2

| Tested results of sample I and sample II of inhalable formulation | | |
|---|---|---|
| Sample Number | Ingredients | Content (%) |
| Sample I | Umeclidinium bromide | 97.97 |
|  | Vilanterol trifenatate | 99.82 |
| Sample II | Umeclidinium bromide | 98.06 |
|  | Vilanterol trifenatate | 98.66 |

Example 3

The preparation of sample III, sample IV and sample V inhalation solution:
The ingredients are listed in table 3. 50% benzalkonium chloride and tween-80 according to table 3, were dissolved in 95% ethanol according to table 3 for three times, and then transferred into 100 ml volumetric flask. Vilanterol trifenatate and umeclidinium bromide according to table 3 were added to the solution, and then sonicated until completely dissolved. Edetate disodium dihydrate according to table 3 was added into the solution, and then sonicated until completely dissolved. Finally, the flask was made to volume with purified water. Sample III, sample IV and sample V solutions remained essentially clear.

The tested results are shown in table 4, which indicate that both vilanterol trifenatate and umeclidinium bromide had been completely dissolved in the solution containing ethanol and tween-80.

TABLE 3

| Ingredient contents of sample III, sample IV and sample V of 100 ml inhalable formulation | | | |
|---|---|---|---|
| Ingredients | Sample III | Sample IV | Sample V |
| Umeclidinium bromide | 21 mg | 21 mg | 21 mg |
| Vilanterol trifenatate | 11 mg | 11 mg | 11 mg |
| Edetate Disodium Dihydrate | 11 mg | 11 mg | 11 mg |
| Tween-80 | 40 mg | 40 mg | 40 mg |
| 50% benzalkonium chloride | 20 mg | 20 mg | 20 mg |
| 95% Ethanol | 20 g | 16 g | 24 g |
| Purified water | Added to 100 ml | Added to 100 ml | Added to 100 ml |

TABLE 4

Tested results of sample III, sample IV and sample V of inhalable formulation

| Sample Number | Ingredients | content (%) |
|---|---|---|
| Sample III | Umeclidinium bromide | 100.00 |
| | Vilanterol trifenatate | 102.08 |
| Sample IV | Umeclidinium bromide | 98.83 |
| | Vilanterol trifenatate | 98.68 |
| Sample V | Umeclidinium bromide | 99.37 |
| | Vilanterol trifenatate | 100.14 |

Example 4

The preparation of sample VI, sample VII and sample VIII inhalation solution:

The ingredients are listed in table 5. 50% benzalkonium chloride and tween-80 according to table 5, were dissolved in 95% ethanol according to table 5 for three times, and then transferred into 100 ml volumetric flask. Vilanterol trifenatate and umeclidinium bromide according to table 5 were added to the solution, and then sonicated until completely dissolved. Edetate disodium dihydrate according to table 5 was added into the solution, and then sonicated until completely dissolved. Finally, the flask was made to volume with purified water. Sample VI, sample VII and sample VIII solutions remained essentially clear.

The tested results were shown in table 6, which indicated that both vilanterol trifenatate and umeclidinium bromide had been completely dissolved in the solution containing ethanol and tween-80.

TABLE 5

Ingredient contents of sample VI, sample VII and sample VIII of 100 ml inhalable formulation

| Ingredients | Sample VI | Sample VII | Sample VIII |
|---|---|---|---|
| Umeclidinium bromide | 21 mg | 21 mg | 21 mg |
| Vilanterol trifenatate | 11 mg | 11 mg | 11 mg |
| Edetate Disodium Dihydrate | 11 mg | 11 mg | 11 mg |
| 50% benzalkonium chloride | 20 mg | 20 mg | 20 mg |
| Tween-80 | 30 mg | 30 mg | 30 mg |
| 95% Ethanol | 16 g | 20 g | 24 g |
| Purified water | Added to 100 ml | Added to | Added to |

TABLE 6

Tested results of sample VI, sample VII and sample VIII of inhalable formulation

| Sample Number | Ingredients | content (%) |
|---|---|---|
| Sample VI | Umeclidinium bromide | 99.59 |
| | Vilanterol trifenatate | 98.09 |
| Sample VII | Umeclidinium bromide | 96.28 |
| | Vilanterol trifenatate | 96.42 |
| Sample VIII | Umeclidinium bromide | 95.42 |
| | Vilanterol trifenatate | 99.59 |

Example 5

The preparation of sample IX and sample X inhalation solution:

The ingredients are listed in table 7. 50% benzalkonium chloride and tween-80 according to table 7, were dissolved in 95% ethanol according to table 7 for three times, and then transferred into 100 ml volumetric flask. Vilanterol trifenatate and umeclidinium bromide according to table 7 were added to the solution, and then sonicated until completely dissolved. Edetate disodium dihydrate according to table 7 was added into the solution, and then sonicated until completely dissolved. Finally, the flask was made to volume with purified water. Sample IX and sample X solutions remained essentially clear.

TABLE 7

Ingredient contents of sample IX and sample X of 100 ml inhalable formulation

| Ingredients | Sample IX | Sample X |
|---|---|---|
| Umeclidinium bromide | 15 mg | 63 mg |
| Vilanterol trifenatate | 8 mg | 33 mg |
| Edetate Disodium Dihydrate | 11 mg | 11 mg |
| Tween-80 | 40 mg | 180 mg |
| 50% benzalkonium chloride | 20 mg | 20 mg |
| 95% Ethanol | 20 g | 20 g |
| Purified water | Added to 100 ml | Added to 100 ml |

Example 6

Aerodynamic Particle Size Distribution:

Sample III was sprayed by a soft mist inhaler. Aerodynamic particle size distribution of droplets of sample III was measured using a Next Generation Impactor (NGI). The Next Generation Impactor operated at a flow rate of 30 L/min was used for determination of particle size distribution. For each of the impactor experiments, the impactor collection stages were coated with a silicone oil. The particle size distribution is expressed in terms of mass median aerodynamic diameter (MMAD) and Geometric Standard Deviation (GSD). The results showed that MMAD of vilanterol trifenatate and umeclidinium bromide were less than 10 The GSD of vilanterol trifenatate and umeclidinium bromide were less than 5% (Table 8).

Example 7

Sample III, sample IV and sample V were sprayed by soft mist inhaler, ultrasonic vibrating mesh nebulizer, and compressed air nebulizer, respectively. A Malvern Spraytec (STP5311) was used to measure the particle size distribution of the droplets. As shown in Table 9, the results indicated that the $D_{50}$ of sample III, sample IV and sample V were less than 10 μm, and the particle size distribution from the soft mist inhaler was more uniform.

TABLE 9

Particle size distribution by using different inhaler or nebulizers

| Sample Number | Partical size (μm) | Using soft mist inhaler | Using compressed air nebulizer | Using ultrasonic vibrating mesh nebulizer |
|---|---|---|---|---|
| Sample III | $D_{10}$ | 2.589 | 1.813 | 2.235 |
| | $D_{50}$ | 5.317 | 4.732 | 5.036 |
| | $D_{90}$ | 10.17 | 10.92 | 11.76 |
| Sample IV | $D_{10}$ | 2.49 | 1.927 | 2.273 |
| | $D_{50}$ | 5.029 | 4.962 | 4.701 |
| | $D_{90}$ | 9.544 | 11 | 9.47 |
| Sample V | $D_{10}$ | 2.729 | 1.857 | 2.091 |
| | $D_{50}$ | 5.276 | 4.092 | 5.149 |
| | $D_{90}$ | 9.554 | 11.15 | 17.55 |

Example 8 to 11

Analogous to Example 1 to 4, benzalkonium chloride is exchanged for sodium benzoate.

Example 12-15

Analogous to Example 1 to 4, benzalkonium chloride is exchanged for benzoic acid.

Example 16-19

Analogous to Example 1 to 4, edetate disodium dihydrate is exchanged for citric acid.

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

What is claimed is:

1. A liquid, propellant-free pharmaceutical preparation consisting of: (a) umeclidinium bromide in an amount ranging from about 15 mg/100 mL to about 50 mg/100 mL and vilanterol trifenatate in an amount ranging from about 8 mg/100 mL to about 30 mg/100 mL; (b) a mixture of water and ethanol wherein the amount of ethanol ranges from about 5% to about 30% (v/v); (c) tween-80 in an amount ranging from about 20 mg/100 mL to about 40 mg/100 mL; and (d) edetate disodium dihydrate in an amount of about 11 mg/100 mL to less than about 20 mg/100 mL; optionally further comprising benzalkonium chloride.

2. A method for administering the pharmaceutical preparation according to claim 1 to a patient, comprising forming an inhalable aerosol by using pressure to force a defined amount of the pharmaceutical preparation through a nozzle to nebulize the pharmaceutical preparation.

3. The method according to claim 2, wherein the defined amount of the pharmaceutical preparation ranges from about 5 to about 30 microliters.

4. The pharmaceutical preparation according to claim 2, which has an aerosol MMAD of less than about 10 μm.

5. The pharmaceutical preparation according to claim 2, which has an aerosol D50 of less than about 10 μm.

6. A method of treating asthma or COPD in a patient, comprising administering to the patient the pharmaceutical preparation according to claim 1.

7. A method for administering the pharmaceutical preparation according to claim 1 to a patient, comprising nebulizing the pharmaceutical preparation in an inhaler, wherein the inhaler includes a block function and counter.

8. The method of claim 7, wherein the patient has asthma or COPD.

9. The method of claim 7, wherein the patient has asthma or COPD.

10. The pharmaceutical preparation according to claim 1, wherein the pharmaceutical preparation is suitable for delivery by soft mist inhalation or nebulization inhalation.

11. A method for administering the pharmaceutical preparation according to claim 1 to a patient, comprising administering the pharmaceutical preparation using a soft mist inhaler.

12. A method for administering the pharmaceutical preparation according to claim 1 to a patient, comprising administering the pharmaceutical preparation using a nebulization inhaler.

13. The pharmaceutical preparation of claim 1 comprising umeclidinium bromide in an amount of about 21 mg/100 mL, vilanterol trifenatate in an amount of about 11 mg/100 mL, tween-80 in an amount of about 40 mg/100 mL, edetate disodium dihydrate in an amount of about 11 mg/100 mL, and ethanol in an amount of about 19% (v/v).

14. The pharmaceutical preparation of claim 13, further comprising 50% benzalkonium chloride in an amount of about 20 mg/100 mL.

15. The pharmaceutical preparation of claim 1 comprising umeclidinium bromide in an amount of about 21 mg/100 mL, vilanterol trifenatate in an amount of about 11 mg/100 mL, tween-80 in an amount of about 40 mg/100 mL, edetate disodium dihydrate in an amount of about 11 mg/100 mL, and ethanol in an amount of about 15% (v/v).

16. The pharmaceutical preparation of claim 15, further comprising 50% benzalkonium chloride in an amount of about 20 mg/100 mL.

17. The pharmaceutical preparation of claim 1 comprising umeclidinium bromide in an amount of about 21 mg/100 mL, vilanterol trifenatate in an amount of about 11 mg/100 mL, tween-80 in an amount of about 40 mg/100 mL, edetate disodium dihydrate in an amount of about 11 mg/100 mL, and ethanol in an amount of about 23% (v/v).

18. The pharmaceutical preparation of claim 17, further comprising 50% benzalkonium chloride in an amount of about 20 mg/100 mL.

19. The pharmaceutical preparation of claim 1 comprising umeclidinium bromide in an amount of about 21 mg/100 mL, vilanterol trifenatate in an amount of about 11 mg/100 mL, tween-80 in an amount of about 30 mg/100 mL, edetate disodium dihydrate in an amount of about 11 mg/100 mL, and ethanol in an amount of about 15% (v/v).

20. The pharmaceutical preparation of claim 19, further comprising 50% benzalkonium chloride in an amount of about 20 mg/100 mL.

21. The pharmaceutical preparation of claim 1 comprising umeclidinium bromide in an amount of about 21 mg/100 mL, vilanterol trifenatate in an amount of about 11 mg/100 mL, tween-80 in an amount of about 30 mg/100 mL, edetate disodium dihydrate in an amount of about 11 mg/100 mL, and ethanol in an amount of about 19% (v/v).

22. The pharmaceutical preparation of claim 12, further comprising 50% benzalkonium chloride in an amount of about 20 mg/100 mL.

23. The pharmaceutical preparation of claim 1 comprising umeclidinium bromide in an amount of about 21 mg/100 mL, vilanterol trifenatate in an amount of about 11 mg/100 mL, tween-80 in an amount of about 30 mg/100 mL, edetate disodium dihydrate in an amount of about 11 mg/100 mL, and ethanol in an amount of about 23% (v/v).

24. The pharmaceutical preparation of claim 23, further comprising 50% benzalkonium chloride in an amount of about 20 mg/100 mL.

* * * * *